United States Patent [19]
Kramer et al.

[11] Patent Number: 6,103,510
[45] Date of Patent: Aug. 15, 2000

[54] HUMAN PHOSPHOLIPASE $A_2$ AND RELATED NUCLEIC ACID COMPOUNDS

[75] Inventors: Ruth Maria Kramer, Indianapolis; Richard Todd Pickard, Noblesville, both of Ind.; John David Sharp, Arlington, Mass.; Beth Ann Strifler, Brownsburg, Ind.

[73] Assignee: Eli Lilly and Company, Indianapolis, Ind.

[21] Appl. No.: 09/045,185

[22] Filed: Mar. 20, 1998

Related U.S. Application Data

[60] Provisional application No. 60/041,571, Mar. 21, 1997.

[51] Int. Cl.[7] .................................................. C12N 9/16
[52] U.S. Cl. ........................ 435/198; 435/69.1; 435/196; 530/350
[58] Field of Search .................... 435/198, 69.1, 435/196; 530/350

[56] References Cited

U.S. PATENT DOCUMENTS

| | | | |
|---|---|---|---|
| 5,045,462 | 9/1991 | Menez et al. | 435/198 |
| 5,328,842 | 7/1994 | Chiou et al. | 435/240.2 |

OTHER PUBLICATIONS

Nalefski et al. (1994) "Delineation of Two Functionally Distinct Domains of Cytosolic Phospholipase A2, a Regulatory Ca2+–dependent Lipid–binding Domain and a Ca2+–independent Catalytic Domain" J. Biol. Chem. 269/27:18239–49.

Nalefski et al. (1996) "Cytosolic Phospholipase A2—Chicken" GB/EMBL/DDBJ Database, Accession No. I50699.

Leslie et al. (1988) "Properties and purification of an arachidonoyl–hydrolyzing phospholipase A2 from a macrophage cell line, RAW 264.7" Biochem. Biophys. Acta 963:476–92.

Molecular weight calculation of polypeptide encoded by SEQ ID No:2 using Intelligenetics PEP–Polypeptide Analysis System Version 5.4. Jan. 13, 1999.

*Primary Examiner*—Robert A. Wax
*Assistant Examiner*—Enrique D. Longton
*Attorney, Agent, or Firm*—Alexander Wilson; Paul J. Gaylo

[57] ABSTRACT

The invention provides a novel phospholipase $A_2$ enzyme, polynucleotides encoding such enzyme and methods for screening unknown compounds for anti-inflammatory activity mediated by the arachidonic acid cascade.

1 Claim, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 2475 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 328..1950

(xi) SEQUENCE DESCRIPTION: SEQ ID NO:1:

```
ACGAGGGGAG GGCTGTTTAA AGGCGCAGGG GCCATTTTAC CTCCAGGTTG GCCCTGCTCA      60

GGACCAGGAG GAAACACCTC CAGCCCGCGA CCTCCTCCCA CAGGGGGAAA AGGAAAGCAG     120

GAGGACCACA GAAGCTTTGG CACCGAGGAT CCCCGCAGTC TTCACCCGCG GAGATTCCGG     180

CTGAAGGAGC TGTCCAGCGA CTACACCGCT AAGCGCAGGG AGCCCAAGCC TCCGCACCGG     240

ATTCCGGAGC ACAAGCTCCA CCGCGCATGC GCACACGCCC CAGACCCAGG CTCAGGAGGA     300

CTGAGAATTT TCTGACCGCA GTGCACC ATG GGA AGC TCT GAA GTT TCC ATA        351
                               Met Gly Ser Ser Glu Val Ser Ile
                                1               5
```

| | | | | | | | | | | | | | | | | |
|---|---|---|---|---|---|---|---|---|---|---|---|---|---|---|---|---|
| ATT | CCT | GGG | CTC | CAG | AAA | GAA | GAA | AAG | GCG | GCC | GTG | GAG | AGA | CGA | AGA | 399 |
| Ile | Pro | Gly | Leu | Gln | Lys | Glu | Glu | Lys | Ala | Ala | Val | Glu | Arg | Arg | Arg | |
|  | 10 |  |  |  | 15 |  |  |  | 20 |  |  |  |  |  |  | |

```
CTT CAT GTG CTG AAA GCT CTG AAG AAG CTA AGG ATT GAG GCT GAT GAG      447
Leu His Val Leu Lys Ala Leu Lys Lys Leu Arg Ile Glu Ala Asp Glu
 25              30                  35                      40

GCC CCA GTT GTT GCT GTG CTG GGC TCA GGC GGA GGA CTG CGG GCT CAC      495
Ala Pro Val Val Ala Val Leu Gly Ser Gly Gly Gly Leu Arg Ala His
                    45                  50                  55

ATT GCC TGC CTT GGG GTC CTG AGT GAG ATG AAA GAA CAG GGC CTG TTG      543
Ile Ala Cys Leu Gly Val Leu Ser Glu Met Lys Glu Gln Gly Leu Leu
                60                  65                  70

GAT GCC GTC ACG TAC CTC GCA GGG GTC TCT GGA TCC ACT TGG GCA ATA      591
Asp Ala Val Thr Tyr Leu Ala Gly Val Ser Gly Ser Thr Trp Ala Ile
            75                  80                  85

TCT TCT CTC TAC ACC AAT GAT GGT GAC ATG GAA GCT CTC GAG GCT GAC      639
Ser Ser Leu Tyr Thr Asn Asp Gly Asp Met Glu Ala Leu Glu Ala Asp
        90                  95                 100

CTG AAA CAT CGA TTT ACC CGA CAG GAG TGG GAC TTG GCT AAG AGC CTA      687
Leu Lys His Arg Phe Thr Arg Gln Glu Trp Asp Leu Ala Lys Ser Leu
105                 110                 115                 120

CAG AAA ACC ATC CAA GCA GCG AGG TCT GAG AAT TAC TCT CTG ACC GAC      735
Gln Lys Thr Ile Gln Ala Ala Arg Ser Glu Asn Tyr Ser Leu Thr Asp
                125                 130                 135

TTC TGG GCC TAC ATG GTT ATC TCT AAG CAA ACC AGA GAA CTG CCG GAG      783
Phe Trp Ala Tyr Met Val Ile Ser Lys Gln Thr Arg Glu Leu Pro Glu
            140                 145                 150

TCT CAT TTG TCC AAT ATG AAG AAG CCC GTG GAA GAA GGG ACA CTA CCC      831
Ser His Leu Ser Asn Met Lys Lys Pro Val Glu Glu Gly Thr Leu Pro
        155                 160                 165

TAC CCG ATA TTT GCA GCC ATT GAC AAT GAC CTG CAA CCT TCC TGG CAG      879
Tyr Pro Ile Phe Ala Ala Ile Asp Asn Asp Leu Gln Pro Ser Trp Gln
    170                 175                 180

GAG GCA AGA GCA CCA GAG ACC TGG TTC GAG TTC ACC CCT CAC CAC GCT      927
Glu Ala Arg Ala Pro Glu Thr Trp Phe Glu Phe Thr Pro His His Ala
185                 190                 195                 200

GGC TTC CCT GCA CTG GGG GCC TTT GTT TCC ATA ACC CAC TTC GGA AGC      975
Gly Phe Pro Ala Leu Gly Ala Phe Val Ser Ile Thr His Phe Gly Ser
                205                 210                 215

AAA TTC AAG AAG GGA AGA CTG GTC AGA ACT CAC CCT GAG AGA GAC CTG     1023
Lys Phe Lys Lys Gly Arg Leu Val Arg Thr His Pro Glu Arg Asp Leu
            220                 225                 230

ACT TTC CTG AGA GGT TTA TGG GGA AGT GCT CTT GGT AAC ACT GAA GTC     1071
Thr Phe Leu Arg Gly Leu Trp Gly Ser Ala Leu Gly Asn Thr Glu Val
        235                 240                 245

ATT AGG GAA TAC ATT TTT GAC CAG TTA AGG AAT CTG ACC CTG AAA GGT     1119
Ile Arg Glu Tyr Ile Phe Asp Gln Leu Arg Asn Leu Thr Leu Lys Gly
    250                 255                 260
```

```
TTA TGG AGA AGG GCT GTT GCT AAT GCT AAA AGC ATT GGA CAC CTT ATT      1167
Leu Trp Arg Arg Ala Val Ala Asn Ala Lys Ser Ile Gly His Leu Ile
265             270                 275                 280

TTT GCC CGA TTA CTG AGG CTG CAA GAA AGT TCA CAA GGG GAA CAT CCT      1215
Phe Ala Arg Leu Leu Arg Leu Gln Glu Ser Ser Gln Gly Glu His Pro
            285                 290                 295

CCC CCA GAA GAT GAA GGC GGT GAG CCT GAA CAC ACC TGG CTG ACT GAG      1263
Pro Pro Glu Asp Glu Gly Gly Glu Pro Glu His Thr Trp Leu Thr Glu
                300                 305                 310

ATG CTC GAG AAT TGG ACC AGG ACC TCC CTG GAA AAG CAG GAG CAG CCC      1311
Met Leu Glu Asn Trp Thr Arg Thr Ser Leu Glu Lys Gln Glu Gln Pro
            315                 320                 325

CAT GAG GAC CCC GAA AGG AAA GGC TCA CTC AGT AAC TTG ATG GAT TTT      1359
His Glu Asp Pro Glu Arg Lys Gly Ser Leu Ser Asn Leu Met Asp Phe
                330                 335                 340

GTG AAG AAA ACA GGC ATT TGC GCT TCA AAG TGG GAA TGG GGG ACC ACT      1407
Val Lys Lys Thr Gly Ile Cys Ala Ser Lys Trp Glu Trp Gly Thr Thr
345             350                 355                 360

CAC AAC TTC CTG TAC AAA CAC GGT GGC ATC CGG GAC AAG ATA ATG AGC      1455
His Asn Phe Leu Tyr Lys His Gly Gly Ile Arg Asp Lys Ile Met Ser
            365                 370                 375

AGC CGG AAG CAC CTC CAC CTG GTG GAT GCT GGT TTA GCC ATC AAC ACT      1503
Ser Arg Lys His Leu His Leu Val Asp Ala Gly Leu Ala Ile Asn Thr
                380                 385                 390

CCC TTC CCA CTC GTG CTG CCC CCG ACG CGG GAG GTT CAC CTC ATC CTC      1551
Pro Phe Pro Leu Val Leu Pro Pro Thr Arg Glu Val His Leu Ile Leu
            395                 400                 405

TCC TTC GAC TTC AGT GCC GGA GAT CCT TTC GAG ACC ATC CGG GCT ACC      1599
Ser Phe Asp Phe Ser Ala Gly Asp Pro Phe Glu Thr Ile Arg Ala Thr
        410                 415                 420

ACT GAT TAC TGC CGC CGC CAC AAG ATC CCC TTT CCC CAA GTA GAA GAG      1647
Thr Asp Tyr Cys Arg Arg His Lys Ile Pro Phe Pro Gln Val Glu Glu
425             430                 435                 440

GCT GAG CTG GAT TTG TGG TCC AAG GCC CCC GCC AGC TGC TAC ATC CTG      1695
Ala Glu Leu Asp Leu Trp Ser Lys Ala Pro Ala Ser Cys Tyr Ile Leu
            445                 450                 455

AAA GGA GAA ACT GGA CCA GTG GTG ATG CAT TTT CCC CTG TTC AAC ATA      1743
Lys Gly Glu Thr Gly Pro Val Val Met His Phe Pro Leu Phe Asn Ile
                460                 465                 470

GAT GCC TGT GGA GGT GAT ATT GAG GCA TGG AGT GAC ACA TAC GAC ACA      1791
Asp Ala Cys Gly Gly Asp Ile Glu Ala Trp Ser Asp Thr Tyr Asp Thr
            475                 480                 485

TTC AAG CTT GCT GAC ACC TAC ACT CTA GAT GTG GTG GTG CTA CTC TTG      1839
Phe Lys Leu Ala Asp Thr Tyr Thr Leu Asp Val Val Val Leu Leu Leu
        490                 495                 500

GCA TTA GCC AAG AAG AAT GTC AGG GAA AAC AAG AAG AAG ATC CTT AGA      1887
Ala Leu Ala Lys Lys Asn Val Arg Glu Asn Lys Lys Lys Ile Leu Arg
505             510                 515                 520

GAG TTG ATG AAC GTG GCC GGG CTC TAC TAC CCG AAG GAT AGT GCC CGA      1935
Glu Leu Met Asn Val Ala Gly Leu Tyr Tyr Pro Lys Asp Ser Ala Arg
            525                 530                 535

AGT TGC TGC TTG GCA TAGATGAGCC TCAGCTTCCA GGGCACTGTG GGCCTGTTGG      1990
Ser Cys Cys Leu Ala
            540

TCTACTAGGG CCCTGAAGTC CACCTGGCCT TCCTGTTCTT CACTCCCTTC AGCCACACGC    2050

TTCATGGCCT TGAGTTCACC TTGGCTGTCC TAACAGGGCC AATCACCAGT GACCAGCTAG    2110

ACTGTGATTT TGATAGCGTC ATTCAGAAGA AGGCGTCCAA GGAGCTGAAG GTGGTGAAAT    2170
```

```
TTGTCCTGCA GGTCCCTCGG GAGATCCTGG AGCTGGAGCA TGAGTGTCTG ACAATCAGAA    2230

GCATCATGTC CAATGTCCAG ATGGCCAGAA TGAATGTGAT AGTTCAGACC AATGCCTTCC    2290

ACTGCTCCTT TATGACTGCA CTTCTAGCCA GTAGCTCTGC ACAAGTTAGC TCTGTAGAAG    2350

TAAGAACTTG GGCTTAAATC ATGGGCTATC TCTCCACAGC CAAGTGGAGC TCTGAGAATA    2410

CAACAAGTGC TCAATAAATG CTTGCTGATT GACTGATGGA AAAAAAAAAA AAAAAAAAA    2470

AAAAA                                                                2475
```

(2) INFORMATION FOR SEQ ID NO:2:

(i) SEQUENCE CHARACTERISTICS:
        (A) LENGTH: 541 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Ser Ser Glu Val Ser Ile Ile Pro Gly Leu Gln Lys Glu Glu
  1               5                  10                  15

Lys Ala Ala Val Glu Arg Arg Leu His Val Leu Ala Leu Lys
             20                  25                  30

Lys Leu Arg Ile Glu Ala Asp Glu Ala Pro Val Ala Val Leu Gly
             35                  40                  45

Ser Gly Gly Gly Leu Arg Ala His Ile Ala Cys Leu Gly Val Leu Ser
         50                  55                  60

Glu Met Lys Glu Gln Gly Leu Leu Asp Ala Val Thr Tyr Leu Ala Gly
 65                  70                  75                  80

Val Ser Gly Ser Thr Trp Ala Ile Ser Ser Leu Tyr Thr Asn Asp Gly
                 85                  90                  95

Asp Met Glu Ala Leu Glu Ala Asp Leu Lys His Arg Phe Thr Arg Gln
                100                 105                 110

Glu Trp Asp Leu Ala Lys Ser Leu Gln Lys Thr Ile Gln Ala Ala Arg
            115                 120                 125

Ser Glu Asn Tyr Ser Leu Thr Asp Phe Trp Ala Tyr Met Val Ile Ser
        130                 135                 140

Lys Gln Thr Arg Glu Leu Pro Glu Ser His Leu Ser Asn Met Lys Lys
145                 150                 155                 160

Pro Val Glu Glu Gly Thr Leu Pro Tyr Pro Ile Phe Ala Ala Ile Asp
                165                 170                 175

Asn Asp Leu Gln Pro Ser Trp Gln Glu Ala Arg Ala Pro Glu Thr Trp
            180                 185                 190

Phe Glu Phe Thr Pro His His Ala Gly Phe Pro Ala Leu Gly Ala Phe
        195                 200                 205

Val Ser Ile Thr His Phe Gly Ser Lys Phe Lys Lys Gly Arg Leu Val
    210                 215                 220

Arg Thr His Pro Glu Arg Asp Leu Thr Phe Leu Arg Gly Leu Trp Gly
225                 230                 235                 240

Ser Ala Leu Gly Asn Thr Glu Val Ile Arg Glu Tyr Ile Phe Asp Gln
                245                 250                 255

Leu Arg Asn Leu Thr Leu Lys Gly Leu Trp Arg Arg Ala Val Ala Asn
            260                 265                 270

Ala Lys Ser Ile Gly His Leu Ile Phe Ala Arg Leu Leu Arg Leu Gln
        275                 280                 285

Glu Ser Ser Gln Gly Glu His Pro Pro Glu Asp Glu Gly Gly Glu
```

```
              290                 295                 300
Pro Glu His Thr Trp Leu Thr Glu Met Leu Glu Asn Trp Thr Arg Thr
305                 310                 315                 320

Ser Leu Glu Lys Gln Glu Gln Pro His Glu Asp Pro Glu Arg Lys Gly
                325                 330                 335

Ser Leu Ser Asn Leu Met Asp Phe Val Lys Lys Thr Gly Ile Cys Ala
            340                 345                 350

Ser Lys Trp Glu Trp Gly Thr Thr His Asn Phe Leu Tyr Lys His Gly
                355                 360                 365

Gly Ile Arg Asp Lys Ile Met Ser Ser Arg Lys His Leu His Leu Val
    370                 375                 380

Asp Ala Gly Leu Ala Ile Asn Thr Pro Phe Pro Leu Val Leu Pro Pro
385                 390                 395                 400

Thr Arg Glu Val His Leu Ile Leu Ser Phe Asp Phe Ser Ala Gly Asp
                405                 410                 415

Pro Phe Glu Thr Ile Arg Ala Thr Thr Asp Tyr Cys Arg Arg His Lys
            420                 425                 430

Ile Pro Phe Pro Gln Val Glu Glu Ala Glu Leu Asp Leu Trp Ser Lys
        435                 440                 445

Ala Pro Ala Ser Cys Tyr Ile Leu Lys Gly Glu Thr Gly Pro Val Val
    450                 455                 460

Met His Phe Pro Leu Phe Asn Ile Asp Ala Cys Gly Gly Asp Ile Glu
465                 470                 475                 480

Ala Trp Ser Asp Thr Tyr Asp Thr Phe Lys Leu Ala Asp Thr Tyr Thr
                485                 490                 495

Leu Asp Val Val Val Leu Leu Leu Ala Leu Ala Lys Lys Asn Val Arg
            500                 505                 510

Glu Asn Lys Lys Lys Ile Leu Arg Glu Leu Met Asn Val Ala Gly Leu
        515                 520                 525

Tyr Tyr Pro Lys Asp Ser Ala Arg Ser Cys Cys Leu Ala
    530                 535                 540

(2) INFORMATION FOR SEQ ID NO:3:

(i) SEQUENCE CHARACTERISTICS:
        (A) LENGTH: 2475 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:3:

ACGAGGGGAG GGCUGUUUAA AGGCGCAGGG GCCAUUUUAC CUCCAGGUUG GCCCUGCUCA      60

GGACCAGGAG GAAACACCUC CAGCCCGCGA CCUCCUCCCA CAGGGGGAAA AGGAAAGCAG    120

GAGGACCACA GAAGCUUUGG CACCGAGGAU CCCCGCAGUC UUCACCCGCG GAGAUUCCGG    180

CUGAAGGAGC UGUCCAGCGA CUACACCGCU AAGCGCAGGG AGCCCAAGCC UCCGCACCGG    240

AUUCCGGAGC ACAAGCUCCA CCGCGCAUGC GCACACGCCC CAGACCCAGG CUCAGGAGGA    300

CUGAGAAUUU UCUGACCGCA GUGCACCAUG GGAAGCUCUG AAGUUUCCAU AAUUCCUGGG    360

CUCCAGAAAG AAGAAAAGGC GGCCGUGGAG AGACGAAGAC UUCAUGUGCU GAAAGCUCUG    420

AAGAAGCUAA GGAUUGAGGC UGAUGAGGCC CCAGUUGUUG CUGUGCUGGG UCAGGCGGA    480

GGACUGCGGG CUCACAUUGC CUGCCUUGGG GUCCUGAGUG AGAUGAAAGA ACAGGGCCUG    540

UUGGAUGCCG UCACGUACCU CGCAGGGGUC UCUGGAUCCA CUUGGGCAAU AUCUUCUCUC    600
```

```
UACACCAAUG AUGGUGACAU GGAAGCUCUC GAGGCUGACC UGAAACAUCG AUUUACCCGA      660

CAGGAGUGGG ACUUGGCUAA GAGCCUACAG AAAACCAUCC AAGCAGCGAG GUCUGAGAAU      720

UACUCUCUGA CCGACUUCUG GGCCUACAUG GUUAUCUCUA AGCAAACCAG AGAACUGCCG      780

GAGUCUCAUU UGUCCAAUAU GAAGAAGCCC GUGGAAGAAG GGACACUACC CUACCCGAUA      840

UUUGCAGCCA UUGACAAUGA CCUGCAACCU UCCUGGCAGG AGGCAAGAGC ACCAGAGACC      900

UGGUUCGAGU UCACCCCUCA CCACGCUGGC UUCCCUGCAC UGGGGGCCUU UGUUUCCAUA      960

ACCCACUUCG GAAGCAAAUU CAAGAAGGGA AGACUGGUCA GAACUCACCC UGAGAGAGAC     1020

CUGACUUUCC UGAGAGGUUU AUGGGGAAGU GCUCUUGGUA ACACUGAAGU CAUUAGGGAA     1080

UACAUUUUUG ACCAGUUAAG GAAUCUGACC CUGAAAGGUU UAUGGAGAAG GGCUGUUGCU     1140

AAUGCUAAAA GCAUUGGACA CCUUAUUUUU GCCCGAUUAC UGAGGCUGCA AGAAAGUUCA     1200

CAAGGGGAAC AUCCUCCCCC AGAAGAUGAA GGCGGUGAGC CUGAACACAC CUGGCUGACU     1260

GAGAUGCUCG AGAAUUGGAC CAGGACCUCC CUGGAAAAGC AGGAGCAGCC CCAUGAGGAC     1320

CCCGAAAGGA AAGGCUCACU CAGUAACUUG AUGGAUUUUG UGAAGAAAAC AGGCAUUUGC     1380

GCUUCAAAGU GGGAAUGGGG GACCACUCAC AACUUCCUGU ACAAACACGG UGGCAUCCGG     1440

GACAAGAUAA UGAGCAGCCG GAAGCACCUC CACCUGGUGG AUGCUGGUUU AGCCAUCAAC     1500

ACUCCCUUCC CACUCGUGCU GCCCCCGACG CGGGAGGUUC ACCUCAUCCU CUCCUUCGAC     1560

UUCAGUGCCG GAGAUCCUUU CGAGACCAUC CGGGCUACCA CUGAUUACUG CCGCCGCCAC     1620

AAGAUCCCCU UCCCCAAGUA GAAGAGGCU GAGCUGGAUU UGUGGUCCAA GGCCCCCGCC     1680

AGCUGCUACA UCCUGAAAGG AGAAACUGGA CCAGUGGUGA UGCAUUUUCC CCUGUUCAAC     1740

AUAGAUGCCU GUGGAGGUGA UAUUGAGGCA UGGAGUGACA CAUACGACAC AUUCAAGCUU     1800

GCUGACACCU ACACUCUAGA UGUGGUGGUG CUACUCUUGG CAUUAGCCAA GAAGAAUGUC     1860

AGGGAAAACA AGAAGAAGAU CCUUAGAGAG UUGAUGAACG UGGCCGGGCU CUACUACCCG     1920

AAGGAUAGUG CCCGAAGUUG CUGCUUGGCA UAGAUGAGCC UCAGCUUCCA GGGCACUGUG     1980

GGCCUGUUGG UCUACUAGGG CCCUGAAGUC CACCUGGCCU UCCUGUUCUU CACUCCCUUC     2040

AGCCACACGC UUCAUGGCCU UGAGUUCACC UUGGCUGUCC UAACAGGGCC AAUCACCAGU     2100

GACCAGCUAG ACUGUGAUUU UGAUAGCGUC AUUCAGAAGA AGGCGUCCAA GGAGCUGAAG     2160

GUGGUGAAAU UUGUCCUGCA GGUCCCUCGG GAGAUCCUGG AGCUGGAGCA UGAGUGUCUG     2220

ACAAUCAGAA GCAUCAUGUC CAAUGUCCAG AUGGCCAGAA UGAAUGUGAU AGUUCAGACC     2280

AAUGCCUUCC ACUGCUCCUU UAUGACUGCA CUUCUAGCCA GUAGCUCUGC ACAAGUUAGC     2340

UCUGUAGAAG UAAGAACUUG GGCUUAAAUC AUGGGCUAUC UCUCCACAGC CAAGUGGAGC     2400

UCUGAGAAUA CAACAAGUGC UCAAUAAAUG CUUGCUGAUU GACUGAUGGA AAAAAAAAA     2460

AAAAAAAAAA AAAAA                                                     2475
```

HUMAN PHOSPHOLIPASE A$_2$ AND RELATED NUCLEIC ACID COMPOUNDS

PRIORITY CLAIM

This application claims the benefit of United States Provisional patent application 60/041,571, filed Mar. 21, 1997.

BACKGROUND OF THE INVENTION

Inflammatory disorders account for a significant number of debilitating diseases. Inflammatory states, such as arthritis, psoriasis, asthma, and possibly atherosclerosis, stem from inflammatory reactions in the joints, skin, and blood vessels. It is generally believed that a central role in the inflammatory reaction is the production of phospholipid metabolites called eicosanoids. The eicosanoids represent a family of important mediators such as the leukotrienes, prostaglandins, lipoxins, hydroxyeicosatetranoic acid, and thromboxanes. It is believed that the generation of eicosanoids is dependent on the availability of arachidonic acid which is liberated from phospholipids by the action of phospholipase A$_2$ (EC 3.1.1.4).

Phospholipase A$_2$ (PLA$_2$) is the common name for phosphatide 2-acylhydrolase, which catalyzes the hydrolysis of the sn-2-acyl ester bond of phosphoglycerides which results in the production of equimolar amounts of lysophospholipids and free fatty acids. see, E. A. Dennis, THE ENZYMES, Vol. 16, Academic Press, New York, (1983). Phospholipase A$_2$ enzymes are found in all living species and form a diverse family of enzymes. Over eighty phospholipase A$_2$ enzymes have been structurally characterized, and they show a high degree of sequence homology. J. Chang, et al., *Biochemical Pharmacology*, 36:2429–2436, (1987); F. F. Davidson and E. A. Dennis, *Journal of Molecular Evolution*, 31:228–238 (1990).

The best characterized varieties of PLA$_2$ enzyme are the secreted forms, which are released into the extracellular environment where they aid in the digestion of biological materials. The secreted forms have a molecular weight of about 12–15,000 (Davidson and Dennis, supra). In contrast, cytosolic phospholipases A$_2$ are found in small amounts within the cell and play a key role in the biosynthetic pathway leading to the formation of the platelet activating factors and the eicosanoids. R. M. Kramer, SIGNAL-ACTIVATED PHOSPHOLIPASES, (M. Liscontdi, ed. 1994) pp. 13–30; J. D. Sharp, et al., *Journal of Biological Chemistry*, 266:14850–14853 (1991).

The cytosolic phospholipases A$_2$ have a molecular weight of approximately 85,000 daltons. J. D. Clark, et al., *Cell*, 65:1043–1051 (1991). Free arachidonic acid is the rate limiting precursor for the production of eicosanoids and is liberated from its membrane phospholipid store by the action of cytosolic PLA$_2$. E. A. Dennis, *Drug Development and Research*, 10:205–220, (1987). The same enzymatic step also produces lysophospholipids which may be converted to platelet-activating factors. Thus, it is believed that cytosolic PLA$_2$ is central to the regulation of the biosynthetic pathways of potent lipid mediators of inflammation.

Recent studies have begun to indicate that a major component of the pathology of Alzheimer's disease is chronic inflammation. See, J. Schnabel, *Science*, 260:1719–1720 (1993). Indeed, pathological investigations have demonstrated the presence of glial hyperactivity, acute phase proteins, and complement factors within affected areas of the brains of persons affected with Alzheimer's disease. Administration of nonsteroidal anti-inflammatory drugs appears to slow the advance of Alzheimer's disease. Id. Understanding this inflammatory component of Alzheimer's disease, therefore, will lead to advances in novel methods of treating patients suffering from this disease.

Due to the central role in the inflammatory component of Alzheimer's disease that appears to be played by phospholipase A$_2$, it is desirable to identify and characterize new inhibitors of this enzyme. The present invention provides a novel phospholipase A$_2$, nucleic acids encoding this enzyme, and assays which may be employed to identify inhibitors having a therapeutic benefit.

```
Met Gly Ser Ser Glu Val Ser Ile Ile Pro Gly Leu Gln Lys Glu Glu
 1               5                  10                  15

Lys Ala Ala Val Glu Arg Arg Arg Leu His Val Leu Lys Ala Leu Lys
                20                  25                  30

Lys Leu Arg Ile Glu Ala Asp Glu Ala Pro Val Val Ala Val Leu Gly
            35                  40                  45

Ser Gly Gly Gly Leu Arg Ala His Ile Ala Cys Leu Gly Val Leu Ser
        50                  55                  60

Glu Met Lys Glu Gln Gly Leu Leu Asp Ala Val Thr Tyr Leu Ala Gly
 65                  70                  75                  80

Val Ser Gly Ser Thr Trp Ala Ile Ser Ser Leu Tyr Thr Asn Asp Gly
                85                  90                  95

Asp Met Glu Ala Leu Glu Ala Asp Leu Lys His Arg Phe Thr Arg Gln
                100                 105                 110

Glu Trp Asp Leu Ala Lys Ser Leu Gln Lys Thr Ile Gln Ala Ala Arg
            115                 120                 125

Ser Glu Asn Tyr Ser Leu Thr Asp Phe Trp Ala Tyr Met Val Ile Ser
        130                 135                 140

Lys Gln Thr Arg Glu Leu Pro Glu Ser His Leu Ser Asn Met Lys Lys
145                 150                 155                 160
```

-continued

```
Pro Val Glu Glu Gly Thr Leu Pro Tyr Pro Ile Phe Ala Ala Ile Asp
                165                 170                 175

Asn Asp Leu Gln Pro Ser Trp Gln Glu Ala Arg Ala Pro Glu Thr Trp
            180                 185                 190

Phe Glu Phe Thr Pro His His Ala Gly Phe Pro Ala Leu Gly Ala Phe
        195                 200                 205

Val Ser Ile Thr His Phe Gly Ser Lys Phe Lys Lys Gly Arg Leu Val
    210                 215                 220

Arg Thr His Pro Glu Arg Asp Leu Thr Phe Leu Arg Gly Leu Trp Gly
225                 230                 235                 240

Ser Ala Leu Gly Asn Thr Glu Val Ile Arg Glu Tyr Ile Phe Asp Gln
                245                 250                 255

Leu Arg Asn Leu Thr Leu Lys Gly Leu Trp Arg Arg Ala Val Ala Asn
            260                 265                 270

Ala Lys Ser Ile Gly His Leu Ile Phe Ala Arg Leu Leu Arg Leu Gln
        275                 280                 285

Gly Ser Ser Gln Gly Glu His Pro Pro Glu Asp Glu Gly Gly Glu
    290                 295                 300

Pro Glu His Thr Trp Leu Thr Glu Met Leu Glu Asn Trp Thr Arg Thr
305                 310                 315                 320

Ser Leu Glu Lys Gln Glu Gln Pro His Glu Asp Pro Glu Arg Lys Gly
                325                 330                 335

Ser Leu Ser Asn Leu Met Asp Phe Val Lys Lys Thr Gly Ile Cys Ala
            340                 345                 350

Ser Lys Trp Glu Trp Gly Thr Thr His Asn Phe Leu Tyr Lys His Gly
        355                 360                 365

Gly Ile Arg Asp Lys Ile Met Ser Ser Arg Lys His Leu His Leu Val
    370                 375                 380

Asp Ala Gly Leu Ala Ile Asn Thr Pro Phe Pro Leu Val Leu Pro Pro
385                 390                 395                 400

Thr Arg Glu Val His Leu Ile Leu Ser Phe Asp Phe Ser Ala Gly Asp
                405                 410                 415

Pro Phe Glu Thr Ile Arg Ala Thr Thr Asp Tyr Cys Arg Arg His Lys
            420                 425                 430

Ile Pro Phe Pro Gln Val Glu Glu Ala Glu Leu Asp Leu Trp Ser Lys
        435                 440                 445

Ala Pro Ala Ser Cys Tyr Ile Leu Lys Gly Glu Thr Gly Pro Val Val
    450                 455                 460

Met His Phe Pro Leu Phe Asn Ile Asp Ala Cys Gly Gly Asp Ile Glu
465                 470                 475                 480

Ala Trp Ser Asp Thr Tyr Asp Thr Phe Lys Leu Ala Asp Thr Tyr Thr
```

```
                            485              490              495
Leu Asp Val Val Leu Leu Leu Ala Leu Ala Lys Lys Asn Val Arg
            500              505              510

Glu Asn Lys Lys Lys Ile Leu Arg Glu Leu Met Asn Val Ala Gly Leu
        515              520              525

Tyr Tyr Pro Lys Asp Ser Ala Arg Ser Cys Cys Leu Ala
    530              535              540
``` hereinafter referred to as SEQ ID NO:2, and having activity as a phospholipase $A_2$. This phospholipase $A_2$ is alternatively referred to as $nPLA_2$ or $PLA_2$-gamma.

The invention also provides an isolated nucleic acid compound that comprises a nucleic acid sequence which encodes the amino acid compounds provided. Particularly this invention provides the isolated nucleic acid compound having the sequence

```
ACGAGGGGAG GGCTGTTTAA AGGCGCAGGG GCCATTTTAC CTCCAGGTTG GCCCTGCTCA    60

GGACCAGGAG GAAACACCTC CAGCCCGCGA CCTCCTCCCA CAGGGGGAAA AGGAAAGCAG   120

GAGGACCACA GAAGCTTTGG CACCGAGGAT CCCCGCAGTC TTCACCCGCG GAGATTCCGG   180

CTGAAGGAGC TGTCCAGCGA CTACACCGCT AAGCGCAGGG AGCCCAAGCC TCCGCACCGG   240

ATTCCGGAGC ACAAGCTCCA CCGCGCATGC GCACACGCCC CAGACCCAGG CTCAGGAGGA   300

CTGAGAATTT TCTGACCGCA GTGCACC ATG GGA AGC TCT GAA GTT TCC ATA       351
                               Met Gly Ser Ser Glu Val Ser Ile
                                1                   5

ATT CCT GGG CTC CAG AAA GAA GAA AAG GCG GCC GTG GAG AGA CGA AGA    399
Ile Pro Gly Leu Gln Lys Glu Glu Lys Ala Ala Val Glu Arg Arg Arg
        10                  15                  20

CTT CAT GTG CTG AAA GCT CTG AAG AAG CTA AGG ATT GAG GCT GAT GAG    447
Leu His Val Leu Lys Ala Leu Lys Lys Leu Arg Ile Glu Ala Asp Glu
 25                  30                  35                  40

GCC CCA GTT GTT GCT GTG CTG GGC TCA GGC GGA GGA CTG CGG GCT CAC    495
Ala Pro Val Val Ala Val Leu Gly Ser Gly Gly Gly Leu Arg Ala His
                    45                  50                  55

ATT GCC TGC CTT GGG GTC CTG AGT GAG ATG AAA GAA CAG GGC CTG TTG    543
Ile Ala Cys Leu Gly Val Leu Ser Glu Met Lys Glu Gln Gly Leu Leu
            60                  65                  70

GAT GCC GTC ACG TAC CTC GCA GGG GTC TCT GGA TCC ACT TGG GCA ATA    591
Asp Ala Val Thr Tyr Leu Ala Gly Val Ser Gly Ser Thr Trp Ala Ile
         75                  80                  85

TCT TCT CTC TAC ACC AAT GAT GGT GAC ATG GAA GCT CTC GAG GCT GAC    639
Ser Ser Leu Tyr Thr Asn Asp Gly Asp Met Glu Ala Leu Glu Ala Asp
     90                  95                 100

CTG AAA CAT CGA TTT ACC CGA CAG GAG TGG GAC TTG GCT AAG AGC CTA    687
Leu Lys His Arg Phe Thr Arg Gln Glu Trp Asp Leu Ala Lys Ser Leu
105                 110                 115                 120

CAG AAA ACC ATC CAA GCA GCG AGG TCT GAG AAT TAC TCT CTG ACC GAC    735
Gln Lys Thr Ile Gln Ala Ala Arg Ser Glu Asn Tyr Ser Leu Thr Asp
                125                 130                 135

TTC TGG GCC TAC ATG GTT ATC TCT AAG CAA ACC AGA GAA CTG CCG GAG    783
Phe Trp Ala Tyr Met Val Ile Ser Lys Gln Thr Arg Glu Leu Pro Glu
            140                 145                 150

TCT CAT TTG TCC AAT ATG AAG AAG CCC GTG GAA GAA GGG ACA CTA CCC    831
Ser His Leu Ser Asn Met Lys Lys Pro Val Glu Glu Gly Thr Leu Pro
        155                 160                 165

TAC CCG ATA TTT GCA GCC ATT GAC AAT GAC CTG CAA CCT TCC TGG CAG    879
Tyr Pro Ile Phe Ala Ala Ile Asp Asn Asp Leu Gln Pro Ser Trp Gln
    170                 175                 180
```

-continued

```
GAG GCA AGA GCA CCA GAG ACC TGG TTC GAG TTC ACC CCT CAC CAC GCT      927
Glu Ala Arg Ala Pro Glu Thr Trp Phe Glu Phe Thr Pro His His Ala
185                 190                 195                 200

GGC TTC CCT GCA CTG GGG GCC TTT GTT TCC ATA ACC CAC TTC GGA AGC      975
Gly Phe Pro Ala Leu Gly Ala Phe Val Ser Ile Thr His Phe Gly Ser
                205                 210                 215

AAA TTC AAG AAG GGA AGA CTG GTC AGA ACT CAC CCT GAG AGA GAC CTG     1023
Lys Phe Lys Lys Gly Arg Leu Val Arg Thr His Pro Glu Arg Asp Leu
                220                 225                 230

ACT TTC CTG AGA GGT TTA TGG GGA AGT GCT CTT GGT AAC ACT GAA GTC     1071
Thr Phe Leu Arg Gly Leu Trp Gly Ser Ala Leu Gly Asn Thr Glu Val
                235                 240                 245

ATT AGG GAA TAC ATT TTT GAC CAG TTA AGG AAT CTG ACC CTG AAA GGT     1119
Ile Arg Glu Tyr Ile Phe Asp Gln Leu Arg Asn Leu Thr Leu Lys Gly
            250                 255                 260

TTA TGG AGA AGG GCT GTT GCT AAT GCT AAA AGC ATT GGA CAC CTT ATT     1167
Leu Trp Arg Arg Ala Val Ala Asn Ala Lys Ser Ile Gly His Leu Ile
265                 270                 275                 280

TTT GCC CGA TTA CTG AGG CTG CAA GAA AGT TCA CAA GGG GAA CAT CCT     1215
Phe Ala Arg Leu Leu Arg Leu Gln Glu Ser Ser Gln Gly Glu His Pro
                285                 290                 295

CCC CCA GAA GAT GAA GGC GGT GAG CCT GAA CAC ACC TGG CTG ACT GAG     1263
Pro Pro Glu Asp Glu Gly Gly Glu Pro Glu His Thr Trp Leu Thr Glu
                300                 305                 310

ATG CTC GAG AAT TGG ACC AGG ACC TCC CTG GAA AAG CAG GAG CAG CCC     1311
Met Leu Glu Asn Trp Thr Arg Thr Ser Leu Glu Lys Gln Glu Gln Pro
            315                 320                 325

CAT GAG GAC CCC GAA AGG AAA GGC TCA CTC AGT AAC TTG ATG GAT TTT     1359
His Glu Asp Pro Glu Arg Lys Gly Ser Leu Ser Asn Leu Met Asp Phe
            330                 335                 340

GTG AAG AAA ACA GGC ATT TGC GCT TCA AAG TGG GAA TGG GGG ACC ACT     1407
Val Lys Lys Thr Gly Ile Cys Ala Ser Lys Trp Glu Trp Gly Thr Thr
345                 350                 355                 360

CAC AAC TTC CTG TAC AAA CAC GGT GGC ATC CGG GAC AAG ATA ATG AGC     1455
His Asn Phe Leu Tyr Lys His Gly Gly Ile Arg Asp Lys Ile Met Ser
                365                 370                 375

AGC CGG AAG CAC CTC CAC CTG GTG GAT GCT GGT TTA GCC ATC AAC ACT     1503
Ser Arg Lys His Leu His Leu Val Asp Ala Gly Leu Ala Ile Asn Thr
                380                 385                 390

CCC TTC CCA CTC GTG CTG CCC CCG ACG CGG GAG GTT CAC CTC ATC CTC     1551
Pro Phe Pro Leu Val Leu Pro Pro Thr Arg Glu Val His Leu Ile Leu
            395                 400                 405

TCC TTC GAC TTC AGT GCC GGA GAT CCT TTC GAG ACC ATC CGG GCT ACC     1599
Ser Phe Asp Phe Ser Ala Gly Asp Pro Phe Glu Thr Ile Arg Ala Thr
            410                 415                 420

ACT GAT TAC TGC CGC CGC CAC AAG ATC CCC TTT CCC CAA GTA GAA GAG     1647
Thr Asp Tyr Cys Arg Arg His Lys Ile Pro Phe Pro Gln Val Glu Glu
425                 430                 435                 440

GCT GAG CTG GAT TTG TGG TCC AAG GCC CCC GCC AGC TGC TAC ATC CTG     1695
Ala Glu Leu Asp Leu Trp Ser Lys Ala Pro Ala Ser Cys Tyr Ile Leu
                445                 450                 455

AAA GGA GAA ACT GGA CCA GTG GTG ATG CAT TTT CCC CTG TTC AAC ATA     1743
Lys Gly Glu Thr Gly Pro Val Val Met His Phe Pro Leu Phe Asn Ile
                460                 465                 470

GAT GCC TGT GGA GGT GAT ATT GAG GCA TGG AGT GAC ACA TAC GAC ACA     1791
Asp Ala Cys Gly Gly Asp Ile Glu Ala Trp Ser Asp Thr Tyr Asp Thr
                475                 480                 485

TTC AAG CTT GCT GAC ACC TAC ACT CTA GAT GTG GTG GTG CTA CTC TTG     1839
Phe Lys Leu Ala Asp Thr Tyr Thr Leu Asp Val Val Val Leu Leu Leu
            490                 495                 500
```

```
                                            -continued
GCA TTA GCC AAG AAG AAT GTC AGG GAA AAC AAG AAG AAG ATC CTT AGA    1887
Ala Leu Ala Lys Lys Asn Val Arg Glu Asn Lys Lys Lys Ile Leu Arg
505                 510                 515                 520

GAG TTG ATG AAC GTG GCC GGG CTC TAC TAC CCG AAG GAT AGT GCC CGA    1935
Glu Leu Met Asn Val Ala Gly Leu Tyr Tyr Pro Lys Asp Ser Ala Arg
                    525                 530                 535

AGT TGC TGC TTG GCA TAGATGAGCC TCAGCTTCCA GGGCACTGTG GGCCTGTTGG    1990
Ser Cys Cys Leu Ala
                540

TCTACTAGGG CCCTGAAGTC CACCTGGCCT TCCTGTTCTT CACTCCCTTC AGCCACACGC   2050

TTCATGGCCT TGAGTTCACC TTGGCTGTCC TAACAGGGCC AATCACCAGT GACCAGCTAG   2110

ACTGTGATTT TGATAGCGTC ATTCAGAAGA AGGCGTCCAA GGAGCTGAAG GTGGTGAAAT   2170

TTGTCCTGCA GGTCCCTCGG GAGATCCTGG AGCTGGAGCA TGAGTGTCTG ACAATCAGAA   2230

GCATCATGTC CAATGTCCAG ATGGCCAGAA TGAATGTGAT AGTTCAGACC AATGCCTTCC   2290

ACTGCTCCTT TATGACTGCA CTTCTAGCCA GTAGCTCTGC ACAAGTTAGC TCTGTAGAAG   2350

TAAGAACTTG GGCTTAAATC ATGGGCTATC TCTCCACAGC CAAGTGGAGC TCTGAGAATA   2410

CAACAAGTGC TCAATAAATG CTTGCTGATT GACTGATGGA AAAAAAAAAA AAAAAAAAA    2470

AAAAA                                                              2475
``` hereinafter referred to as SEQ ID NO:1.

The present invention also provides processes for producing a phospholipase enzyme, said process comprising: (a) establishing a culture of the host cell transformed with an nPLA$_2$ encoding polynucleotide in a suitable culture medium; and (b) isolating said enzyme from said culture. Compositions comprising a peptide made according to such processes are also provided.

The present invention also provides methods for identifying an inhibitor of phospholipase activity, said method comprising: (a) combining a phospholipid, a candidate inhibitor compound, and a composition comprising a protein of the present invention; and (b) observing whether said protein of the present invention cleaves said phospholipid and releases fatty acid thereby. Inhibitors of phospholipase activity identified by such methods, pharmaceutical compositions comprising a therapeutically effective amount of such inhibitors and a pharmaceutically acceptable carrier, and methods of reducing inflammation by administering such pharmaceutical compositions to a mammalian subject are also provided.

Polyclonal and monoclonal antibodies to the peptides of the invention are also provided.

DETAILED DESCRIPTION AND PREFERRED EMBODIMENTS

The terms and abbreviations used in this document have their normal meanings unless otherwise designated. For example "_C" refers to degrees Celsius; "N" refers to normal or normality; "mmol" refers to millimole or millimoles; "g" refers to gram or grams; "ml" means milliliter or milliliters; "M" refers to molar or molarity; "μg" refers to microgram or micrograms; and "μl" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and (deoxy)thymidine, respectively, when they occur in DNA molecules. The abbreviations U,C,G, and A correspond to the 5'-monophosphate forms of the ribonucleosides uridine, cytidine, guanosine, and adenosine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. To insure against improper translation, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter to control transcription of the inserted DNA has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., MOLECULAR CLONING: A LABORATORY MANUAL, (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other phospholipase $A_2$ variants. This term may also be employed in the sense that such antibodies may be used to differentiate between the human phospholipase $A_2$ protein and analogous proteins derived from other species.

The term "PCR" as used herein refers to the widely-known polymerase chain reaction employing a thermally-stable polymerase.

The phospholipase $A_2$ enzymes comprise a widely distributed family of enzymes which catalyze the hydrolysis of the acyl ester bond of glycerophospholipids at the sn-2 position. One kind of phospholipase $A_2$ enzymes, secreted phospholipase $A_2$, or "14 kD secreted s$PLA_2$", are involved in a number of biological functions, including phospholipid digestion, the toxic activities of numerous venoms, and potential antibacterial activities. A second kind of phospholipase $A_2$ enzymes, the intracellular phospholipase $A_2$ enzymes, also known as cytosolic phospholipase $A_2$ or c$PLA_2$, are active in membrane phospholipid turnover and in regulation of intracellular signaling mediated by the multiple components of the well-known arachidonic acid cascade. One or more c$PLA_2$ enzymes are believed to be responsible for the rate limiting step in the arachidonic acid cascade, namely, release of arachidonic acid from membrane glycerophospholipids. The action of c$PLA_2$ also results in biosynthesis of platelet activating factor (PAF).

The phospholipase B enzymes are a family of enzymes which catalyze the hydrolysis of the acyl ester bond of glycerophospholipids at the sn-1 and sn-2 positions. The mechanism of hydrolysis is unclear but may consist of initial hydrolysis of the sn-2 fatty acid followed by rapid cleavage of the sn-1 substituent, i.e., functionally equivalent to the combination of phospholipase $A_2$ and lysophospholipase (Salto, et al., *Methods of Enzymology*, 1991, 197:446; Gassama-Diagne, et al., *Journal of Biological Chemistry*, 1989, 264:9470). Whether these two events occur at the same or two distinct active sites has not been resolved. It is also unknown if these enzymes have a preference for the removal of unsaturated fatty acids, in particular arachidonic acid, at the sn-2 position and, accordingly, contribute to the arachidonic acid cascade.

Upon release from the membrane, arachidonic acid may be metabolized via the cyclooxygenase pathway to produce the various prostaglandins and thromboxanes, or via the lipoxygenase pathway to produce the various leukotrienes and related compounds. The prostaglandins, leukotrienes and platelet activating factor are well known mediators of various inflammatory states, and numerous anti-inflammatory drugs have been developed which function by inhibiting one or more steps in the arachidonic acid cascade. Use of the present anti-inflammatory drugs which act through inhibition of arachidonic acid cascade steps has been limited by the existence of side effects which may be harmful to various individuals.

A very large industrial effort has been made to identify additional anti-inflammatory drugs which inhibit the arachidonic acid cascade. In general, this industrial effort has employed the secreted phospholipase $A_2$ enzymes in inhibitor screening assays, for example, as disclosed in U.S. Pat. No. 4,917,826. However, because the secreted phospholipase $A_2$ enzymes are extracellular proteins (i.e., not cytosolic) and are not specific for hydrolysis of arachidonic acid, they are presently not believed to participate directly in the arachidonic acid cascade. While some inhibitors of the small secreted phospholipase $A_2$ enzymes have anti-inflammatory action, such as indomethacin, bromphenacyl bromide, mepacrine, and certain butyrophenones as disclosed in U.S. Pat. No. 4,239,780, it is presently believed that inhibitor screening assays should employ cytosolic phospholipase $A_2$ enzymes which directly participate in the arachidonic acid cascade.

An improvement in the search for anti-inflammatory drugs which inhibit the arachidonic acid cascade was developed in commonly assigned U.S. Pat. No. 5,322,776, incorporated herein by reference. In that application, a cytosolic form of phospholipase $A_2$ was identified, isolated, and cloned. Use of the cytosolic form of phospholipase $A_2$ to screen for anti-inflammatory drugs provides a significant improvement in identifying inhibitors of the arachidonic acid cascade. The cytosolic phospholipase $A_2$ disclosed in U.S. Pat. No. 5,322,776 is a 110 kD protein which depends on the presence of elevated levels of calcium inside the cell for its activity. The $cPLA_2$ of U.S. Pat. No. 5,322,776 plays a pivotal role in the production of leukotrienes and prostaglandins initiated by the action of pro-inflammatory cytokines and calcium mobilizing agents. The $cPLA_2$ of U.S. Pat. No. 5,322,776 is activated by phosphorylation on serine residues and increasing levels of intracellular calcium, resulting in translocation of the enzyme from the cytosol to the membrane where arachidonic acid is selectively hydrolyzed from membrane phospholipids.

In addition to the $cPLA_2$ of U.S. Pat. No. 5,322,776, some cells contain calcium independent phospholipase $A_2$ (and/or phospholipase B) enzymes. For example, such enzymes have been identified in rat, rabbit, canine and human heart tissue (Gross, *TCM*, 1991, 2:115; Zupan, et at., *Journal of Medicinal Chemistry*, 1993, 36: 95; Hazen, et al., Journal of Clinical Investigators, 1993, 91:2513; Lehman, et al, *Journal of Biological Chemistry*, 1993, 268:20713; Zupan, et al., *Journal of Biological Chemistry*, 1992, 267:8707; Hazen, et al., *Journal of Biological Chemistry*, 1991, 266:14526; Loeb, et al., *Journal of Biological Chemistry*, 1986, 261:10467; Wolf, et al., *Journal of Biological Chemistry*, 1985, 260:7295; Hazen, et al., *Methods in Enzymology*, 1991, 197:400; Hazen, et al., *Journal of Biological Chemistry*, 1990, 265:10622; Hazen, a al., *Journal of Biological Chemistry*, 1993, 268:9892; Ford, et al., *Journal of Clinical Investigators*, 1991, 88:331; Hazen, et al., *Journal of Biological Chemistry*, 1991, 266:5629; Hazen, et al., *Circulation Research*, 1992, 70:486; Hazen, et al., *Journal of Biological Chemistry*, 1991, 266:7227; Zupan, et al., *FEBS*, 1991, 284:27), as well as rat and human pancreatic islet cells (Ramanadham, et al., *Biochemistry*, 1993, 32:337; Gross, et al, *Biochemistry*, 1993, 32:327), in the macrophage-like cell line, P388D1 (Ulevitch, et al., *Journal of Biological Chemistry*, 1988, 263:3079; Ackermann, et al., *Journal of Biological Chemistry*, 1994, 269:9227; Ross, et al., *Arch. Biochem. Biophys.*, 1985, 238:247; Ackermann, et al., *FASEB Journal*, 1993, 7(7): 1237), in various rat tissue cytosols (Nijssen, et al., *Biochim. Biophys. Acta*, 1986, 876:611; Pierik, et al., *Biochim. Biophys. Acta*, 1988, 962:345; Aarsman, et al., *Journal of Biological Chemistry*, 1989, 264:10008), bovine brain (Ueda, et al., *Biochem. Biophys. Res. Comm.*, 1993, 195:1272; Hirashima, et al., *Journal of Neurochemistry*, 1992, 59:708), in yeast (*Saccharomyces cerevisiae*) mitochondria (Yost, et al, *Biochemistry International*, 1991, 2–4:199), hamster heart cytosol (Cao, et al., *Journal of Biological Chemistry*, 1987, 262:16027), rabbit lung microsomes (Angle, et al., *Biochim. Biophys. Acta*, 1988, 962:234) and guinea pig intestinal brush-border membrane (Gassama-Diagne, et al., *Journal of Biological Chemistry*, 1989, 264:9470).

It is believed that the calcium independent phospholipase $A_2$/B enzymes may perform important functions in release of arachidonic acid in specific tissues which are characterized by unique membrane phospholipids, by generating lysophospholipid species which are deleterious to membrane integrity or by remodeling of unsaturated species of membrane phospholipids through deacylation/reacylation mechanisms. The activity of such a phospholipase may well be regulated by mechanisms that are different from that of the $cPLA_2$ of U.S. Pat. No. 5,322,776. In addition the activity may be more predominant in certain inflamed tissues over others. Although the enzymatic activity is not dependent on calcium this does not preclude a requirement for calcium in vivo, where the activity may be regulated by the interaction of other protein(s) whose function is dependent upon a calcium flux.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See. e.g., H. Dugas and C. Penney, BIOORGANIC CHEMISTRY, (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology*, 68:109 (1979). See also, J. Sambrook, et al, supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
| --- | --- |
| DH5α | F−(φ80dlacZΔM15), Δ(lacZYA-argF)U169 supE44, λ−, hsdR17($r_K^-$, $m_K^+$), recA1, endA1, gyrA96, thi-1, relA1 |
| HB101 | supE44, hsdS20($r_B^- m_B^-$), recA13, ara-14, proA2 lacY1, galK2, rpsL20, xyl-5, mtl-1, mcrB, mrr |
| JM109 | recA1, e14−(mcrA), supE44, endA1, hsdR17($r_K^-$, $m_K^+$), gyrA96, relA1, thi-1, Δ(lac-proAB), F'[traD36, proAB + lacI^q,lacZΔM15] |
| RR1 | supE44, hsdS20($r_B^- m_B^-$), ara-14 proA2, lacY1, galK2, rpsL20, xyl-5, mtl-5 |
| χ1776 | F−, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cyCA1, hsdR2, λ− |
| 294 | endA, thi−, hsr−, $hsm_k^+$ (U.S. Pat. 4,366,246) |
| LE392 | F−, hsdR514 (r−m−), supE44, supF58, lacY1, or Δlac(1-Y)6, galK2, glaT22, metB1, trpR55, λ− |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of *E. coli* employed in the cloning and expression of the genes of this invention is RV308, which is available from the ATCC under accession number ATCC 31608, and is described in U.S. Pat. No. 4,551,433, issued Nov. 5, 1985.

In addition to the strains of *E. coli* discussed supra, bacilli such as *Bacillus subtilis*, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., *Nature* (*London*), 275:615 (1978); and Goeddel et al., *Nature* (*London*), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human phospholipase $A_2$-encoding nucleic acids of the present invention. Exemplary host cells suitable for use in the present invention are listed in Table I

TABLE I

| Host Cell | Origin | Source |
| --- | --- | --- |
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embryonal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-644 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See. e.g., J. Schimke, Cell, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., Proceedings of the National Academy of Sciences (USA), 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. No. 5,242,688, issued Sep. 7, 1993, and U.S. Pat. No. 4,992,373, issued Feb. 12, 1991, all of which are herein incorporated by reference. Escherichia coli K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See. eg, L. Stinchcomb, et al., *Nature (London)*, 282:39 (1979); J. Kingsman et al., *Gene*, 7:141 (1979); S. Tschemper et al., *Gene,* 10:157 (1980). This plasmid already contains the !M gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec-hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile Leu, Val | |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human phospholipase $A_2$ molecule may be produced using synthetic methodology. This synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See. e.g., M. J. Gait, ed., OLIGONUCLEOTIDE SYNTHESIS, A PRACTICAL APPROACH, (1984).

The synthetic human phospholipase $A_2$ gene of the present invention may be designed to possess restriction endonuclease cleavage sites at either end of the transcript to facilitate isolation from and integration into expression and amplification plasmids. The restriction sites are chosen so as to properly orient the coding sequence of the target enzyme with control sequences to achieve proper in-frame reading and expression of the phospholipase $A_2$ molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid compounds described supra the present invention also encompasses the ribonucleic acid compounds having the following sequence

```
ACGAGGGGAG GGCUGUUUAA AGGCGCAGGG GCCAUUUUAC CUCCAGGUUG GCCCUGCUCA    60
GGACCAGGAG GAAACACCUC CAGCCCGCGA CCUCCUCCCA CAGGGGGAAA AGGAAAGCAG   120
GAGGACCACA GAAGCUUUGG CACCGAGGAU CCCCGCAGUC UUCACCCGCG GAGAUUCCGG   180
CUGAAGGAGC UGUCCAGCGA CUACACCGCU AAGCGCAGGG AGCCCAAGCC UCCGCACCGG   240
AUUCCGGAGC ACAAGCUCCA CCGCGCAUGC GCACACGCCC CAGACCCAGG CUCAGGAGGA   300
CUGAGAAUUU UCUGACCGCA GUGCACCAUG GGAAGCUCUG AAGUUUCCAU AAUUCCUGGG   360
CUCCAGAAAG AAGAAAAGGC GGCCGUGGAG AGACGAAGAC UUCAUGUGCU GAAAGCUCUG   420
AAGAAGCUAA GGAUUGAGGC UGAUGAGGCC CCAGUUGUUG CUGUGCUGGG CUCAGGCGGA   480
GGACUGCGGG CUCACAUUGC CUGCCUUGGG GUCCUGAGUG AGAUGAAAGA ACAGGGCCUG   540
UUGGAUGCCG UCACGUACCU CGCAGGGGUC UCUGGAUCCA CUUGGGCAAU AUCUUCUCUC   600
UACACCAAUG AUGGUGACAU GGAAGCUCUC GAGGCUGACC UGAAACAUCG AUUUACCCGA   660
CAGGAGUGGG ACUUGGCUAA GAGCCUACAG AAAACCAUCC AAGCAGCGAG GUCUGAGAAU   720
UACUCUCUGA CCGACUUCUG GGCCUACAUG GUUAUCUCUA AGCAAACCAG AGAACUGCCG   780
GAGUCUCAUU UGUCCAAUAU GAAGAAGCCC GUGGAAGAAG GGACACUACC CUACCCGAUA   840
UUUGCAGCCA UUGACAAUGA CCUGCAACCU UCCUGGCAGG AGGCAAGAGC ACCAGAGACC   900
UGGUUCGAGU UCACCCCUCA CCACGCUGGC UUCCCUGCAC UGGGGGCCUU UGUUUCCAUA   960
ACCCACUUCG GAAGCAAAUU CAAGAAGGGA AGACUGGUCA GAACUCACCC UGAGAGAGAC  1020
CUGACUUUCC UGAGAGGUUU AUGGGGAAGU GCUCUUGGUA ACACUGAAGU CAUUAGGGAA  1080
UACAUUUUUG ACCAGUUAAG GAAUCUGACC CUGAAAGGUU UAUGGAGAAG GGCUGUUGCU  1140
AAUGCUAAAA GCAUUGGACA CCUUAUUUUU GCCCGAUUAC UGAGGCUGCA AGAAAGUUCA  1200
CAAGGGGAAC AUCCUCCCCC AGAAGAUGAA GGCGGUGAGC CUGAACACAC CUGGCUGACU  1260
GAGAUGCUCG AGAAUUGGAC CAGGACCUCC CUGGAAAAGC AGGAGCAGCC CCAUGAGGAC  1320
CCCGAAAGGA AAGGCUCACU CAGUAACUUG AUGGAUUUG UGAAGAAAAC AGGCAUUUGC  1380
GCUUCAAAGU GGGAAUGGGG GACCACUCAC AACUUCCUGU ACAAACACGG UGGCAUCCGG  1440
GACAAGAUAA UGAGCAGCCG GAAGCACCUC CACCUGGUGG AUGCUGGUUU AGCCAUCAAC  1500
ACUCCCUUCC CACUCGUGCU GCCCCCGACG CGGGAGGUUC ACCUCAUCCU CUCCUUCGAC  1560
UUCAGUGCCG GAGAUCCUUU CGAGACCAUC CGGGCUACCA CUGAUUACUG CCGCCGCCAC  1620
```

```
                                    -continued
AAGAUCCCCU  UUCCCCAAGU  AGAAGAGGCU  GAGCUGGAUU  UGUGGUCCAA  GGCCCCCGCC    1680

AGCUGCUACA  UCCUGAAAGG  AGAAACUGGA  CCAGUGGUGA  UGCAUUUUCC  CCUGUUCAAC    1740

AUAGAUGCCU  GUGGAGGUGA  UAUUGAGGCA  UGGAGUGACA  CAUACGACAC  AUUCAAGCUU    1800

GCUGACACCU  ACACUCUAGA  UGUGGUCGUG  CUACUCUUGG  CAUUAGCCAA  GAAGAAUGUC    1860

AGGGAAAACA  AGAAGAAGAU  CCUUAGAGAG  UUGAUGAACG  UGGCCGGGCU  CUACUACCCG    1920

AAGGAUAGUG  CCCGAAGUUG  CUGCUUGGCA  UAGAUGAGCC  UCAGCUUCCA  GGGCACUGUG    1980

GGCCUGUUGG  UCUACUAGGG  CCCUGAAGUC  CACCUGGCCU  UCCUGUUCUU  CACUCCCUUC    2040

AGCCACACGC  UUCAUGGCCU  UGAGUUCACC  UUGGCUGUCC  UAACAGGGCC  AAUCACCAGU    2100

GACCAGCUAG  ACUGUGAUUU  UGAUAGCGUC  AUUCAGAAGA  AGGCGUCCAA  GGAGCUGAAG    2160

GUGGUGAAAU  UUGUCCUGCA  GGUCCCUCGG  GAGAUCCUGG  AGCUGGAGCA  UGAGUGUCUG    2220

ACAAUCAGAA  GCAUCAUGUC  CAAUGUCCAG  AUGGCCAGAA  UGAAUGUGAU  AGUUCAGACC    2280

AAUGCCUUCC  ACUGCUCCUU  UAUGACUGCA  CUUCUAGCCA  GUAGCUCUGC  ACAAGUUAGC    2340

UCUGUAGAAG  UAAGAACUUG  GGCUUAAAUC  AUGGGCUAUC  UCUCCACAGC  CAAGUGGAGC    2400

UCUGAGAAUA  CAACAAGUGC  UCAAUAAAUG  CUUGCUGAUU  GACUGAUGGA  AAAAAAAAAA    2460

AAAAAAAAAA  AAAAA                                                        2475
``` hereinafter referred to as SEQ ID NO:3, or the complementary ribonucleic acid, or a fragment of either SEQ ID NO:3 or the complement thereof. The ribonucleic acids of the present invention may be prepared using the polynucleotide synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which is SEQ ID NO:1, SEQ ID NO:3 or a complementary sequence of SEQ ID NO:1 or SEQ ID NO:3, or a fragment thereof, and which is at least 18 base pairs in length, and which will selectively hybridize to genomic DNA or messenger RNA encoding a phospholipase $A_2$, is provided. Preferably, the 18 or more base pair compound is DNA.

The term "selectively hybridize" as used herein may refer to either of two situations. In the first such embodiment of this invention, the nucleic acid compounds described supra hybridize DNA or RNA encoding a human phospholipase $A_2$ under more stringent hybridization conditions than these same nucleic acid compounds would hybridize to an analogous phospholipase $A_2$ of another species, e.g. murine or primate. In the second such embodiment of this invention, these probes hybridize to DNA or RNA encoding a phospholipase $A_2$ of the present invention under more stringent hybridization conditions than other related compounds, including nucleic acid sequences encoding other human phospholipase $A_2$ enzymes.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:2.

Yet another embodiment of the invention is a method of using a nPLA$_2$-encoding gene to transform a cell. There is a wide variety of transformation techniques applicable to both prokaryotic and eukaryotic cells which will not be discussed, because such methods are old in the art.

A further embodiment of the invention consists of a method of using a host cell to express nPLA$_2$. In this embodiment, a host cell, either prokaryotic or eukaryotic, that has been transformed is cultured in an appropriate medium until a substantial cell mass has been obtained. Fermentation of transformed prokaryotes and mass cell culture of transformed eukaryotic cells is well known in the art and will not be discussed for that reason.

The second step of this embodiment is the isolation of nPLA$_2$ from the cultured cells. Two methods for purifying cPLA$_2$ from a non-transformed mammalian cell line are described in U.S. Pat. No. 5,328,842, the entire contents of which are herein incorporated by reference. The following summarizes those methods.

Once grown and harvested, the cultured cells are lysed by nitrogen cavitation in the presence of protease inhibitors. A soluble fraction is prepared from the lysate by ultracentrifugation. The resulting solution of cytosolic proteins contains cPLA$_2$ and is subjected to a series of purification procedures.

The soluble fraction of the cell lysate is run through a series of column chromatography procedures. Anion exchange chromatography is followed by hydrophobic interaction, molecular sizing and finally another hydrophobic interaction technique where the conditions are such that the cPLA$_2$ binds the resin weakly. Each column is run individually, and the eluate is collected in fractions while monitoring for absorbance at 280 nm. Fractions are assayed for phospholipase $A_2$ activity, and those fractions with the desired activity are then run over the next column until a homogeneous solution of $cPLA_2$ is obtained.

Immunoaffinity purification using anti-$PLA_2$ antibodies is an alternative to the series of chromatographic procedures already mentioned. Making antiserum or monoclonal antibodies directed against a purified protein is well known in the art, and skilled artisans readily will be able to prepare anti-$PLA_2$ antibodies. Preparing an immunoaffinity matrix using such antibodies and isolating $PLA_2$ using the immunoaffinity matrix is also well within the skill of the art. See, AFFINITY CHROMATOGRAPHY PRINCIPLES & METHODS, Pharmacia Fine Chemicals, 1983.

The invention also encompasses a method of using a $nPLA_2$-encoding gene to screen compounds. By using purified, recombinantly, or even naturally produced $nPLA_2$, it is possible to test whether a particular compound is able to inhibit or block $nPLA_2$ enzyme activity. By adding the test compound over a wide range of concentrations to the substrate solution described in Example 1 below, it is trivial to determine whether a given compound is able to inhibit or block the enzyme's activity.

The following examples will help describe how the invention is practiced and will illustrate the characteristics of the claimed $nPLA_2$-encoding genes, vectors, host cells, and methods of the invention.

EXAMPLE 1

$nPLA_2$ Enzymatic Activity Assay

The substrate, sonicated liposomes containing phosphatidylethanolamine ([$^{14}$C]PE, 55 mCi/mmol from NEN Research Products) and sn-1,2-dioleoylglycerol (DG, Avanti Polar Lipids, Birmingham, Ala.) at a molar ratio of 2:1, is prepared as follows. [$^{14}$C]PE (20 nmol, $1\times10^6$ dpm, 50 $\mu$Ci/ml in toluene/ethanol) and DG (10 nmol, 100 $\mu$g/ml in chloroform) are dried under nitrogen. The lipids are dispersed in 1 ml of 150 mM NaCl, 50 mM HEPES, pH 7.5 (assay buffer) by sonication at 4° C., with a Microson probe-sonicator (Heat Systems Ultrasonics) for 4×15 seconds, with 45 second intervals. Bovine serum albumin (essentially fatty acid free, from a 100 mg/ml stock in water, Sigma) is added to a final concentration of 4 mg/ml. Samples to be assayed for $nPLA_2$ activity are incubated with 50 $\mu$l liposomes (0.5 nmol [$^{14}$C]PC, 50,000 dpm containing 0.25 nmol of DG) in a total volume of 0.2 ml of assay buffer containing 1 mM $CaCl_2$ and 1 mM 2-mercaptoethanol. Incubations are carried out at 37° C. for 15 minutes and terminated by adding 2 ml of Dole's reagent (2-propanol/heptane/0.5M sulfuric acid, 40:10:1 containing 10 $\mu$g/ml of stearic acid). After mixing, 1.2 ml of heptane and 1 ml of water are added. The mixtures are briefly vortexed and the upper phase transferred to tubes containing 2 ml of heptane and 150 mg of BIO-SIL™ (Bio-Rad Laboratories), activated at 130° C. before use. The tubes are thoroughly vortexed and centrifuged (1000×g for 5 minutes). The supernatants are decanted into scintillation vials. After addition of 10 ml of a liquid scintillation cocktail (Ready Protein +, Beckman) radioactivity is counted using a Beckman liquid scintillation counter Model LS 7000. High radioactive counts correlate with enzymatic activity.

Repetitions of this study have shown $nPLA_2$ to have enzymatic activity using phosphatidylethanolamine as a substrate, but not when phosphatidylcholine is employed as a substrate.

EXAMPLE 2

Eukaryotic Expression of $nPLA_2$

Transient expression of $nPLA_2$ is achieved in the human embryonal kidney cell line 293. The line is a permanent part of the American Type Culture Collection (ATCC) and is available under accession number CRL 1573.

A) Plasmid Isolation

One half liter of DS broth (12 gm tryptone, 24 gm yeast extract, 4 ml glycerol, 100 ml of 0.17M $KH_2PO_4$+0.72M $K_2HPO_4$ per liter) containing 100 $\mu$g/ml ampicillin is inoculated with E. coli K12 DH5 alpha cells containing a suitable vector of the present invention and incubated in an air shaker at 37° C. overnight.

The culture is then removed and centrifuged in a Sorvalt GSA rotor (Dupont Co., Instrument Products, Newtown, Conn. 06470) at 7500 rpm for 10 minutes at 4° C. The resulting supernatant is discarded, and the cell pellet is resuspended in 14 mls of a solution of 25% sucrose and 50 mM Tris/HCl (Sigma), pH 8.0; the mixture is then transferred to an oakridge tube. Two milliliters of a 10 mg/ml lysozyme solution and 0.75 ml of 0.5M ethylene diamine tetraacetic acid (EDTA) pH 8.4, are added to the solution, which is then incubated on ice for 15 minutes. 1.5 mls of Triton lytic mix (3% Triton X-100 (Sigma), 0.19M EDTA, 0.15M Tris/HCl pH 8.0) is added to the solution, which is then incubated for 15 minutes. The solution is centrifuged in a Sorvall SS34 rotor (Dupont Co., Instrument products, Newtown, Conn. 06470) at 20,000 rpm for 45 minutes at 40° C. The resulting supernatant containing plasmid DNA is removed and mixed with a solution of 20.55 g CsCl, 0.28 ml of 1M Tris/HCl pH 8.0, and 1.35 ml of a 10 mg/ml ethidium bromide (EtBr) solution. The final volume of the mixture is brought to 27 ml with water. The mixture is centrifuged in two Quick-seal tubes (Beckman Cat. #342413) in a Ti 75 rotor (Beckman Instruments, Inc.) at 45,000 rpm for 4 days at 20° C. Plasmid bands are collected separately into two new Quick-seal tubes. One hundred fifty microliters of EtBr (10 mg/ml) is added into each tube and then the tubes are topped off with a $CsCl/H_2O$ (double distilled, deionized water) solution (density=1.56 g/ml) and centrifuged in a Ti 75 rotor at 45,000 rpm for 24 hours at 20° C.

The plasmid band is collected and an equal volume of water is added to dilute the CsCl. Ethidium bromide is extracted 5 times with between 2 and 3 volumes of 1-butanol. Absolute ethanol (2.5 volumes) is added to the extracted solution containing plasmid, which is incubated at room temperature for 5–10 minutes and then centrifuged in a Soyall SS34 rotor at 10,000 rpm for 10 minutes. The DNA pellet is dried and then dissolved in 200 $\mu$l of TE solution (1 mM EDTA, 10 mM Tris/HCl pH 8.0).

B) Transfection of Eukaryotic Cell Line 293

One day prior to transfection, 293 cells are seeded in two, 100 $cm^2$ culture dishes (Falcon #1005) at a density of $1\times10^6$ cells per dish. The cells are seeded and grown in DMEM (Dulbecco's Modified Eagle Medium; GIBCO, Grand Island, N.Y.) supplemented with 10% fetal bovine serum (Hyclone; Ogden, Utah) and 50 mg/ml of gentamycin (GIBCO) in a 5% carbon dioxide, humidified 37° C. incubator. Approximately 20 $\mu$g of purified plasmid DNA is added to a calcium phosphate transfection buffer (see Wigler, et al., Proceedings of the National Academy of Sciences (USA), 76, (1979) in the absence of any carrier DNA. The transfection is allowed to proceed for four hours at 37° C., after which the transfection buffer is replaced with DMEM, supplemented as described above, and the cells are allowed to grow for three days.

C) Cell Lysis

The transfected cultures are washed once with wash buffer (140 mM NaCl, 5 mM KCl, 2 mM EDTA, 25 mM HEPES, pH 7.4) and are removed from the culture dishes by adding 10 ml of wash buffer followed by scraping. The cells (approximately 1×10⁷) are placed in a conical tube and centrifuged. One milliliter of wash buffer plus 1 mM phenylmethane sulfonyl fluoride, 100 µM leupeptin and 100 µM pepstatin A is added to the pellet and the cells are lysed using a probe sonicator (Model W-385, Heat Systems Ultrasonics) with a stepped microtip at an output setting of 1. Sonication is repeated six times for 15 seconds at 45 second intervals.

The transfected 293 lysates are then assayed for nPLA$_2$ activity according to Example 1.

EXAMPLE 3
Stable Eukaryotic Expression of cPLA$_2$

Stable expression of cPLA$_2$ is achieved in the human embryonal kidney cell line 293 and in the AV12 hamster cell line. The AV12 cell line is a permanent part of the ATCC and is available under accession number CRL9595, and the 293 cell line is a permanent part of the ATCC and is available under accession number CRL1573. Plasmids containing the nPLA$_2$-encoding gene are prepared according to Example 2 A).

Both mammalian cell lines are transfected with an appropriate plasmid according to Example 2B) except that the plasmid DNA is first linearized by digestion with an appropriate restriction enzyme and precipitated with ethanol. After transfection, both cell lines are individually seeded into culture plates and grown for three days in DMEM after which the medium is replaced with selective medium (e.g., DMEM supplemented as described above plus 200 ug/ml hygromycin) to kill any cells which did not take up the linearized plasmid DNA.

After 5 days, most of the originally seeded cells will have spontaneously detached from the culture plates and are removed by the weekly changes of medium (twice weekly for AV12 cells); however, colonies will grow from both cell lines. These colonies are transferred to 24-well trays (Costar Inc.) using plastic pipet tips.

The transfected lines are grown and assayed as described in Examples 1 and 2. The negative controls are the non-transformed cell lines handled in the same fashion. The results clearly show that stable cell lines expressing nPLA$_2$ are obtained by transformation with vectors of the invention.

EXAMPLE 5
Western Blot Analysis

Immunological and electrophoretic equivalence between naturally-occurring cPLA$_2$, described in U.S. Pat. No. 5,328,842, and recombinant nPLA$_2$ produced using one of the DNA sequences of the present invention, is established by western blot analysis.

Monoclonal antibodies specific for cPLA$_2$ are described in U.S. Pat. No. 5,328,842. One of those antibodies is used as the primary antibody to probe the blot for cPLA$_2$ in the present example. The primary antibody, at a concentration of 0.5 mg/ml, is diluted 1:570 in TBST plus 0.02% sodium azide. The protein-containing blot is incubated overnight at 4° C. in the primary antibody solution and then washed as before.

The blot is then reacted with a secondary antibody by incubating it for 6 hours at room temperature in a solution of immunoaffinity purified rabbit anti-mouse IgG antibody (commercially available) diluted 1:5000 in TBST. The blot is then washed as before, followed by incubation at 4° C. overnight in a 1:500 dilution (TBST) of goat anti-rabbit IgG conjugated to horseradish peroxidase. The blot is washed and developed for 60 minutes at room temperature in a solution of 42 ml of 0.1M phosphate buffer, pH 6; 8 mls of 4-chloronapthol (3 mg/ml in methanol) containing 300 uls of 3% hydrogen peroxide.

DNA Sequencing

Sequence determinations are performed with dideoxy chain termination with an automated flourescent dye DNA sequencer (Applied Biosystems) or manually using [α-³⁵S] dATP followed by autoradiography. For manual sequencing either a T7 primer or a M13F (forward) primer is used.

Generation of a PCR Probe for Screening of Library

A PCR product is generated with the PLA$_2$ clone as a template with primers appropriately chosen under the following conditions: 1 minute at 94° C., 1 minute at 55° C. and 2 minutes at 72° C. for 25 cycles. The product is labeled with [α-³²P]dCTP using a random priming method. The probe is purified on a SEPHADEX G-50™ column to remove non-incorporated nucleotides.

Screening of a Human Genomic Library

A human genomic DNA library made from lymphocytes in a commercially available lambda vector, lambda DASH™, is plated out with *E. coli* LE 392 as bacterial host strain. Hybridizations are carried out for 16 hours with high stringency at 65° C. in 25% formamide, 6× SSC, 10% Dextran sulfate, 5× Denhardt's solution and 0.1% SDS. Plaques are lifted with nylon membranes. Filters are washed twice at room temperature in 2× SSC, 0.5% SDS and twice for 30 minutes at 65° C. in 0.2× SSC, 0.5% SDS. The filters are exposed on film. Screenings are carried out in three consecutive steps and single plaques are picked in the tertiary screening. A number of strongly hybridizing plaques are selected and a high titer stock is made for amplification of the phages.

Phage Clone Characterization

Phages are grown in *E. coli* LE 392 in liquid culture. Phage particles are collected and DNA is extracted and digested with various restriction enzymes and run on agarose gel. The gel is denatured and blotted onto a nylon membrane. The membrane is hybridized as described above with the rat probe and exposed on film. Hybridizing fragments are identified and cloned into the commonly used plasmid vector Bluescript KS+. Plasmid DNA is prepared using commercially available kits. A restriction map is constructed for overlapping hybridizing clones.

Cloning into Expression Vector

If no suitable restriction sites are available in the PLA$_2$ clone for cloning into the expression vector, two oligonucleotides may be used as primers to generate a fragment containing the entire coding region, or a substantial segment thereof, employing PCR technology.

The PCR is run with VENT DNA POLYMERASE™ (a commercially available DNA polymerase cloned from the archaebacterium *Thermococcus litoralis*, New England Biolabs, Beverly, Mass.) and the PLA$_2$ clone as a template under the following conditions: 1 minute at 94° C., 1 minute at 50° C. and 2 minutes at 72° C. for 25 cycles. An aliquot of the PCR reaction is run on an agarose gel and displays the expected product of 1.25 kb. The remainder of the reaction is phenol extracted, cut with the appropriate restriction enzymes and run on a preparative agarose gel and collected onto a DEAE membrane. The DNA is eluted from the membrane and purified by phenol extraction. The fragment is then ligated into the expression vector.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The desired plasmid may be isolated from E. coli containing these plasmids using standard procedures such as cesium chloride DNA isolation or isolation in a QIAGEN™ column.

Any plasmid comprising the gene of the present invention is readily modified to construct expression vectors that produce phospholipase $A_2$ in a variety of organisms, including, for example, E. coli, Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, CURRENT PROTOCOLS IN MOLECULAR BIOLOGY, 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oligonucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for E. coli can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and E. coli cells which have been transfected and/or transformed with a vector which comprises a nucleic acid of the present invention.

The present invention also provides a method for constructing a recombinant host cell capable of expressing SEQ ID NO:3, said method comprising transforming a host cell with a recombinant DNA vector that comprises an isolated DNA sequence which encodes SEQ ID NO:3. The preferred host cell is AV12. The preferred vector for expression is one which comprises SEQ ID NO:1. Another preferred host cell for this method is E. coli. An especially preferred expression vector in E. coli is one which comprises SEQ ID NO:1. Transformed host cells may be cultured under conditions well known to skilled artisans such that SEQ ID NO:1 is expressed, thereby producing the phospholipase $A_2$ in the recombinant host cell.

The ability of an agent to inhibit the protein of the present invention is essential in the development of a multitude of indications. In developing agents which act as inhibitors of phospholipase $A_2$, it would be desirable, therefore, to determine those agents which interact with the protein of the present invention. Generally, such an assay includes a method for determining whether a substance is a functional ligand of phospholipase $A_2$, said method comprising contacting a functional compound of the phospholipase $A_2$ with said substance, monitoring enzymatic activity by physically detectable means, and identifying those substances which effect a chosen response.

The instant invention provides such a screening system useful for discovering agents which inhibit the phospholipase $A_2$, said screening system comprising the steps of:

a) isolating a phospholipase $A_2$;
b) exposing said phospholipase $A_2$ to a potential inhibitor of the phospholipase $A_2$;
c) quantifying the activity of the phospholipase $A_2$ relative to a control in which no potential inhibitor is introduced.

This allows one to rapidly screen for inhibitors of phospholipase $A_2$. Utilization of the screening system described above provides a sensitive and rapid means to determine compounds which inhibit phospholipase $A_2$. This screening system may also be adapted to automated procedures such as a PANDEX® (Baxter-Dade Diagnostics) system allowing for efficient high-volume screening of potential therapeutic agents.

Pharmaceutical compositions containing anti-inflammatory agents (i.e., inhibitors) identified by the screening method of the present invention may be employed to treat, for example, a number of inflammatory conditions such as rheumatoid arthritis, psoriasis, asthma, inflammatory bowel disease and other diseases mediated by increased levels of prostaglandins, leukotriene, or platelet activating factor. Pharmaceutical compositions of the invention comprise a therapeutically effective amount of a $nPLA_2$ inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 µg to about 100 mg per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See. e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e g. J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', Fab2', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See. e.g., C. Milstein, HANDBOOK OF EXPERIMENTAL IMMUNOLOGY, (Blackwell Scientific Pub., 1986); J. Goding, MONOCLONAL ANTIBODIES: PRINCIPLES AND PRACTICE, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate india single anti, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Pat. No. Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See. e.g. R. E. Bird, et al., Science 242:423–426 (1988); PCT Publication No. WO 88/01649, which was published Mar. 10, 1988; U.S. Pat. No. 5,260,203, issued Nov. 9, 1993, the entire contents of which are herein incorporated by reference. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of phospholipase $A_2$.

In addition to being functional as direct therapeutic and diagnostic aids, the availability of a family of antibodies which are specific for phospholipase $A_2$ enables the development of numerous assay systems for detecting agents which bind to this receptor. One such assay system comprises radiolabeling phospholipase $A_2$-specific antibodies with a radionuclide such as $^{125}I$ and measuring displacement of the radiolabeled phospholipase $A_2$-specific antibody from solid phase phospholipase $A_2$ in the presence of a potential inhibitor.

Numerous other assay systems are also readily adaptable to detect agents which bind phospholipase $A_2$. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for phospholipase $A_2$, this invention also provides antibodies which are specific for the hypervariable regions of the phospholipase $A_2$ antibodies. Some such anti-idiotypic antibodies would resemble the original epitope, the phospholipase $A_2$, and, therefore, would be useful in evaluating the effectiveness of compounds which are potential inhibitors of the phospholipase $A_2$. See. e.g., Cleveland, et al., *Nature* (*London*), 305:56 (1983); Wasserman, et al., *Proceedings of the National Academy of Sciences* (*USA*), 79:4810 (1982).

In another embodiment, this invention encompasses pharmaceutical formulations for parenteral administration which contain, as the active ingredient, the anti-phospholipase $A_2$ antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

Immunocytochemistry

Immunocytochemistry has demonstrated increased numbers of reactive astrocytes containing cytosolic phospholipase $A_2$ in the astrocytes of brains from patients suffering from Alzheimer's disease. See, U.S. Pat. No. 5,478,857, issued Dec. 26, 1995, the entire contents of which are herein incorporated by reference. Immunochemistry is performed on paraffin sections from human occipital cortex of persons afflicted with Alzheimer's disease as well as normal persons. In each case the tissue is fixed only briefly (60–90 minutes) and then transferred to Tris-buffered saline for several days prior to embedding. The monoclonal antibody M12 is raised against purified $cPLA_2$ from U937 cells using standard techniques. Ascites are produced in BALB/c mice and antibodies are affinity-purified using Protein A Fast Flow™ resin. The antibody M12 recognizes the native form of $cPLA_2$ and is also a neutralizing antibody. A rabbit antiserum to glial fibrillary acidic protein (GFAP; Biogenex Labs, San Ramon, Calif.) is used to label astrocytes.

Immunostaining of tissue sections (10 $\mu$M) utilizes conventional immunoperoxidase techniques and employed the avidin-biotin peroxidase system (ABC, Vector Laboratories, Burlingame, Calif.). For $cPLA_2$ localization, 0.1 mg/ml M12 antibody is used. Anti-GFAP is obtained as prediluted antisera. Dual localization is carried out by sequential immunostaining. An alkaline phosphatase-streptavidin system (Biogenex Labs) using Fast Red™ as chromagen is used to localize the rabbit antibody (GFAP) and nickel chloride-enhanced DAB (Vector Laboratories) is used to detect the peroxidase-labeled mouse anti-$cPLA_2$.

These immunochemistry studies demonstrate localization of $cPLA_2$ in protoplasmic astrocytes in the gray matter and provide further evidence for the importance of this cell type in inflammatory processes in the brain. Comparison of normal adult brains with those brains from persons afflicted with Alzheimer's disease evinces the role of cytosolic phospholipase $A_2$ in the inflammatory component of this disease.

We claim:

1. An isolated human phospholipase $A_2$ which comprises the amino acid sequence of SEQ ID NO:2.

* * * * *